United States Patent [19]

Schweighardt et al.

[11] Patent Number: 4,781,676

[45] Date of Patent: Nov. 1, 1988

[54] INTERSTITIAL ADMINISTRATION OF PERFLUOROCHEMICAL EMULSIONS FOR REOXYGENATION OF HYPOXIC TUMOR CELLS

[75] Inventors: Frank K. Schweighardt, Allentown; David V. Woo, Downingtown, both of Pa.

[73] Assignee: Air Products and Chemicals, Inc., Allentown, Pa.

[21] Appl. No.: 16,812

[22] Filed: Feb. 20, 1987

[51] Int. Cl.$^4$ .............................. A61N 1/30
[52] U.S. Cl. ........................ 604/21; 604/51; 128/362; 128/804; 514/34; 600/1
[58] Field of Search .................. 604/19-21, 604/49, 51; 128/362, 422, 1 R, 1.3, 1.1, 1.2, 804; 424/320-325; 514/34

[56] References Cited

U.S. PATENT DOCUMENTS

| | | | |
|---|---|---|---|
| 4,325,772 | 4/1982 | Geyer et al. | 424/325 |
| 4,558,690 | 12/1985 | Joyce | 128/1 R |
| 4,686,085 | 8/1987 | Osterholm | 604/21 |
| 4,742,050 | 5/1988 | Yuhos et al. | 514/34 |

FOREIGN PATENT DOCUMENTS

| | | |
|---|---|---|
| 0089815 | 3/1983 | European Pat. Off. . |
| 7701991 | 8/1977 | Netherlands ............ 604/51 |

OTHER PUBLICATIONS

Martin et al; "Enhancement of Tumor Radiation Response by the Combination of a Perfluorochemical Emulsion and Hyperbaric Oxygen"; 5-87; Int. J. Radiation Oncology Biology Physics 13:5, pp. 747-751.

King et al; "Peripheral Vascular Responses to Fluorocarbon Administration", Microvascular Research; 33, 183-193 (1987).

T. Kokunai et al; "Effect of Perfluorochemicals on BLNU Chemotherapy in Rat Brain Tumor Model", Brain & Nerve 1982, 34(6), 609-615.

Author (Rockwell/Mate/Irvin & Nierenburg), Date-2/6/86, Title (Reactions of Tumors & Normal Tissues to Irradiation in the Presence and Absense of a Perfluorochemical Emulsion.

Author (McIntosh), Date-12/11/86, Title (Process for Treating Metastasis of Cancerous Tumors).

Author (Yuhus), Date-8/10/83, Title (Perfluorocarbon Emulsions & Their Preparation & Use in Therapy).

Author (Rockwell), Date-8/17/84, Title (Use of a Perfluorochemical Emulsion to Improve Oxygenation in a Solid Tumor).

Author (Brown), Date-1984, Title (Sensitizers & Protectors to Radiation & Chemotherapeutic Drugs).

Author (Lustig & McIntosh), Date-1986, Title (Fluosol$^R$-DA in Radiation Therapy).

Primary Examiner—C. Fred Rosenbaum
Assistant Examiner—Mario Costantino
Attorney, Agent, or Firm—Geoffrey L. Chase; William F. Marsh; James C. Simmons

[57] ABSTRACT

A method is set forth for treatment of hypoxic tumors by interstitial injection of oxygen bearing fluorocarbon emulsions directly into the hypoxic zone of the tumor followed by radiation treatment.

17 Claims, 3 Drawing Sheets

INTERSTITIAL ADMINISTRATION OF PERFLUOROCHEMICAL EMULSIONS FOR REOXYGENATION OF HYPOXIC TUMOR CELLS

TECHNICAL FIELD

The present invention is directed to a method of treatment of mammalian cancers or tumors using oxygen bearing perfluorochemicals and radiation therapy.

BACKGROUND OF THE PRIOR ART

The medical and health care profession has administered therapeutic radiation treatments to animals and human patients to reduce, slow down or affect the growth of or to achieve the destruction of various cancers or tumors affecting such animals or patients. A recognition of the medical health profession to the lack of efficacy of radiation on certain tumors has arisen. Specifically, species of tumors exist wherein due to rapid growth rate or other characteristics, an oxygen depleted or hypoxic zone exists within the tumor. Such hypoxic cells are not amenable to traditional radiation therapy without incurring such severe conditions so as to endanger healthy tissues. To overcome this lack of efficacy in radiation therapy various means for administering oxygen to hypoxic tumors has been described in the prior art.

R. A. Lustig and N. L. McIntosh in Transfusion Medicine: Recent Technological Advances, page 29 through 38, 1986 demonstrated the use of Fluosol-DA to enhance the effect of radiation on animal tumors. They require 100% oxygen be given the animal through respiration for 72 hours after receiving 8–16 ml/kg of Fluosol-DA administered intravenously. The treated animals are then subjected to photon radiation after the intravenous injection.

S. Rockwell in International Journal of Radiation Oncology, Biology and Physics volume 11, pages 97 through 103. 1985 demonstrated the use of Fluosol-DA to improve oxygenation in solid tumors. The Fluosol-DA was injected intravenously into animals at the rate of 15 ml/kg. The author found that the presence of the fluorochemical did enhance the effect of radiation therapy.

J. M. Brown, et al. in Cancer Treatment Symposia, volume 1, page 85, 1984 proposed the use of fluorochemical emulsions to enhance the effect of radio therapy for tumor treatment. No work accompanied the proposal to demonstrate the overall effect of such a proposal.

C. W. Song. et al. in International Journal of Radiation Oncology. Biology and Physics, volume 11. pages 1833 to 1836. 1985 demonstrated the increased radio sensitivity of tumors using perfluorochemicals as an intravenous injection into animals which were simultaneously breathing a carbogen atmosphere.

J. M. Yuhas. et al. in International Patent Application No. W084/00686 filed Mar. 1, 1984 teaches the use of a fluorochemical as diagnostic and oxygen carrier agents in the examination or treatment, respectively, of hypoxic tumors or as an intravenous adjuvant with an added drug or agent. The patent mentions intramuscular administration or injection at or near the site of hypoxia but teaches away from this by reciting that "direct contact" is ideal but "may not be achievable and in fact is not required."

Sara Rockwell, Timothy P. Mate, Caroline G. Irvin, and Mary Ann Nieremburg report in International Journal of Radiation Oncology. Biology, and Physics, volume 12, pages 1315 to 1318, 1986 the treatment of mice with a Fluosol-DA emulsion to heighten favorable response of radiation therapy on mammary tumors. The test mice did not show favorable enhancement when breathing air or nitrogen or when breathing carbogen alone without Fluosol emulsion injected intravenously. Only when Fluosol emulsion was injected intravenously while the mice breathed a carbogen-containing atmosphere did enhanced radio therapy efficacy become observed.

N. L. McIntosh in published European Patent Application No. 0201275 of Nov. 12, 1986 discloses a therapy of cancerous tumors by injecting multiple doses of perfluorocarbon emulsion into a patient and simultaneously having the patient breathe an oxygen-enriched atmosphere. In light of the oxygen-enriched breathing the McIntosh therapy necessarily involves vascular circulation of the emulsion to the lungs. Radiation or chemotherapy is then administered to the patient after the emulsion has carried oxygen from the lungs to the vicinity of the tumor. The emulsion is administered in an amount of from 2 to 15 ml per kg of body weight, preferably 4–10 ml/kg.

All of the above described procedures utilize injections that require circulation through the lungs or vascular system in order to carry oxygen to the tumor and therefore to enhance radiation therapy effects.

BRIEF SUMMARY OF THE INVENTION

The present invention is a method of treating hypoxic mammalian tumor cells comprising administering an oxygenated fluorocarbon emulsion interstitially directly into said tumor cell mass and thereafter subjecting the administered cells to an amount of radiation effective to initiate destruction of said cells.

Preferably the radiation treatment is performed promptly after administration of the emulsion.

Preferably, the fluorocarbon is oxygen saturated and is selected from the perfluorocarbon group consisting of perfluoroperhydrophenanthrene perfluoro n-butyldecalin and mixtures thereof.

Preferably the emulsion comprises a perfluorocarbon with a vapor pressure less than 5 torr. selected from partially or fully condensed $C_9$–$C_{14}$ perfluoro compounds present in the emulsion in the concentration of 10–90 wt./vol. %. a surfactant selected from the group of lecithins, acetylenic diols polyoxyethylene-polyoxypropylene polymers, a mixture of lecithin, glycerin, monoglycerides or triglycerides or combinations of the above surfactants with the remainder of the emulsion being an aqueous phase wherein the emulsion has a particle size range of 0.005 to 0.20 microns.

Preferably the radiation comprises x-rays in the dose of above approximately 500 and up to 5,000 rads administered up to 15 minutes after the administration of the emulsion.

Alternatively, the method can be performed in a series of emulsion administrations, each followed by radiation treatment or an emulsion administration followed by a series of radiation treatments over a period of time.

Preferably the perfluorochemical emulsion is administered in an amount no greater than 0.055 ml/kg of the patient's body weight.

DETAILED DESCRIPTION OF THE DRAWING

DETAILED DESCRIPTION OF THE INVENTION

Previously it has been suggested and demonstrated that intravascular administration of fluorochemical emulsions may aid to increase the availability of molecular oxygen to convert hypoxic tumor cells to radio sensitive tumor cells prior to radiation therapy. In addition, localized thermal treatment has been used to induce more oxygen at the site of the tumor cells. Both methods have been applied clinically.

Such techniques have arisen from the problem in treatment of many mammalian tumors which have necrotic zones that strongly suggests the presence of hypoxic cells, which when presented with molecular oxygen revert to radio sensitive cells and consequently become targets for radiation treatment that destroys them. No direct method of supplying molecular oxygen to such hypoxic cells has been demonstrated to date prior to the present invention. The present invention uses a fully oxygenated fluorochemical emulsion to interstitially administer directly into mammalian tumors, such as malignant melanomas, such that 10-50% of the tumor volume is infused with the emulsion. The tumors are immediately (up to 15 minutes) irradiated with 500 to 2,500 rads of radiation (10 to 30 $G_y$ of 10-20 NeV photons). The solublized oxygen oxygenates the hypoxic tumor cells and acts as a adjuvant for photon radiation therapy for more effective radiation cell kill. This direct interstitial introduction of oxygen-rich fluorochemical emulsions into the hypoxic zone of the tumor provides high concentrations of localized oxygen for hypoxic tumor cells that have marginal vascular blood/oxygen supply. Therefore, the present invention provides oxygen readily for radiation therapy, which in intravascular applications of the prior art can not supply sufficient oxygen for the same level of effect for radiation treatment. The present invention, in effect, allows for a more rapid and direct transfer of soluble oxygen to the centers of radio resistant hypoxic tumors cells than the intravascular means or thermal excitation of the prior art.

The theory as to why the present invention provides an efficacious therapy treatment of improved degree over traditional intravenous therapies is based upon the proposed understanding of the activity of oxygen and radiation. Ionizing radiation has been used in the treatment of cancer and tumors for over 80 years. Photon radiation can cause cell destruction by indirect interaction through the formation of chemically reactive free radicals. For this to occur, oxygen must be present. Short lived free radicals are formed when both radiation and oxygen are present in tissue. These free radicals interact with the intracellular nucleic acid molecules (DNA, RNA) causing damage which will lead to cell death. Oxygen must be present at the precise moment of radiation therapy. If a tumor grows rapidly enough, it will outstrip its vascular supply thereby reducing the amount of oxygen to its cells. When the cells have less oxygen to sustain normal metabolism, they become oxydeficient or hypoxic. If the oxygen deficiency becomes too great, then these cells will die, forming necrotic zones. These hypoxic cell populations found in rapidly growing mammalian tumors around necrotic zones are radiation resistant. They do not respond as well to radiation induced cell kill as normal fully oxygenated cells. Such hypoxic cells require 2-3 fold increase in the radiation dose to achieve similar cell death as normal oxygenated tumor cells.

In light of this problem, the present invention provides a therapeutic approach by which oxygen can be made readily available to the immediate area of hypoxic tumor cells to provide the necessary oxygen content for effective radiation therapy, resulting in the destruction of such cells. The present invention utilizes a method for the direct administration, i.e. interstitial, of an oxygenated perfluorochemical emulsion to the site of the hypoxic zone of the tumor where oxygen deprivation, i.e. the hypoxic condition, exists. This differs from the intravenous administration of the prior art. Such direct interstitial administration of the oxygenated emulsion provides an unexpected effect on the reduction of tumor growth by increasing tumor doubling time.

In order to qualify as an appropriate fluorochemical emulsion or microemulsion, emulsions used in the present invention must be biocompatible with normal tissue and cells. An emulsion pH of 6.8 is achieved by acid/base titration or preferably by the use of non-toxic isotonic buffers with sufficient buffering capacity to maintain the desired acidity. The emulsion particle size may range from 0.005 to 0.20 microns, preferably 0.005 to 0.08 microns. Particles of larger size (greater than 0.1) and specifically those above 0.2 microns are undesirable, as they tend to aggregate and may lose their ability to distribute themselves throughout the subject tumor mass. Preparation of the emulsion may be performed by homogenization, sonication, ultra-mixing, microfluidization or spontaneous mixing as in microemulsions. The preferred method of formation of the emulsion is microfluidization because more absolute control of the particle size is achievable with a minimum of energy input per unit volume of emulsion prepared. The concentration of the perfluorochemical can range from 10 to 90 weight/volume % with the preferred concentration being in the range of 25 to 75 weight/volume %. Concentrations less than 10 weight/volume % are ineffective, and concentrations greater than 90 weight/volume % are unstable for long term storage as a pharmaceutical supply, but are nonetheless effective on incidental clinical basis. The fluorochemical emulsion administration dosage is preferably in the range of 0.009 to 0.055 ml/kg of emulsion based on body weight although it is possible to administer a dosage up to the equivalent of 50% of the tumor volume, but less than 2 ml/kg of emulsion based upon body weight.

The fluorochemical ingredient of the emulsion used in the methology of the present invention should be comprised entirely of fluorine and carbon, with the presence of various heteroatoms (N, O, S) not favored in the order N>S>O because of the high potential for toxic side products to remain after purification of the fluorocarbon. The fluorocarbon should have a vapor pressure of less than 5 torr. to substantially reduce in vivo vaporization during treatment to the tumor site. It is preferred that the fluorochemical have vapor pressure of less than 1 torr. for optimum performance, based upon an evaluation of perfluorochemicals with a range of vapor pressures between 0.1 to 22 torr. The ideal fluorochemical is a fully fluorinated condensed $C_{14}$ material, such as perfluoroperhydrophenanthrene or partially condensed perfluoro C-4, C-5, C-6 alkyldecalins, such as perfluoro n-butyl decalin.

The fluorochemical emulsion used in the method of the present invention requires a surfactant to emulsify the fluorochemical in an aqueous phase. Appropriate surfactants include egg yolk lecithin and other phosphatides, as well as commercial synthetic materials such as SURFYNOL® SE surfactant, PLURONIC® P-105 surfactant, and LIPOSYN® II nutrient emulsion, as well as PLURONIC® F-68 surfactant. Preferably. SURFYNOL® SE surfactant and PLURONIC® P-105 surfactant in 0.2/0.28% mixture is utilized. SURFYNOL® SE surfactant is an acetylenic polyol that is available from Air Products and Chemicals, Inc. Allentown, PA. PLURONIC® F-68 and P-105 surfactants are ethylene and propylene oxide polymers that are available from Wyandotte Corp.. Wyandotte, Mich. LIPOSYN®II (10% and 20%) emulsion is a lecithin and glyceride nutrient that is available from Abbott Laboratories, North Chicago. Ill.

An appropriate emulsion was formulated using a mixture of 85% perfluoroperhydrophenanthrene and 15% perfluoro n-butyldecalin. The fluorocarbon mixture itself has the following physical chemical properties reported in Table I.

TABLE I

| Fluorochemical Physical Properties | | |
|---|---|---|
| Boiling Point | 215° C. | 491° F. |
| Pour Point | −48° C. | −54° F. |
| Heat Capacity, 25° C. | 0.17 Cal/g °C. | 0.17 Btu/lb °F. |
| Density, 25° C. | 2.01 g/ml | 125.4 lbs/ft$^3$ |
| Thermal Conductivity, 25° C. | 0.040 cal/hr cm$^2$ °C. | 0.032 Btu/hr °F. ft |
| Ag. Mol. Wt. | 630 g/mole | 630 lbs/mole |
| Heat of Vaporization | 16.1 Cal/g | 29 Btu/lb. |
| Kinematic Viscosity, 25° C. | 7.4 cs | 0.29 ft$^2$/hr |
| Surface Tension | 21 dynes/cm | 0.0014 lbs/ft |
| Vapor Pressure, 25° C. | 0.10 torr | 0.002 psia |
| Coefficient of Expansion | 0.0014 cm$^2$/cm$^3$ °C. | 0.0008 in$^3$/in$^3$ °F. |
| Refractive Index, 25° C. | 1.3338 | 1.3338 |
| Dielectric Constant, 25° C. (1 KHz) | 1.94 | 1.94 |
| Dielectric Strength, 25° C. | 118 Kvolts/cm | 300 volts/mil |

A 67 weight/volume % emulsion was prepared using 4 weight volume % of supercritically extracted egg yolk lecithin in lactated Ringer's solution and the above described fluorochemical mixture. The lecithin (250 mg) was initially dissolved in 2 to 3 milliliters of chloroform which was evaporated off using nitrogen or argon in order to coat the sides of the glass test tube. 4 mil of ice cold (4° C.) lactated Ringer's solution was added to the preparation vessel and the mixture sonicated at a low energy setting for 4 to 6 seconds. The perfluoro chemical (2 mil chilled to 4° C.) was then injected rapidly using a syringe and needle into the lecithin Ringer's solution while sonicating at a medium energy. Finally, the emulsion was sonicated at high energy three times for six to eight seconds, allowing at least one minute between sonications. Particle size measurements were made on a Nicomp laser light scattering device and determined to be 0.08 microns with a distribution of plus or minus 0.02 microns. This emulsion was used in the experiments demonstrating the subject invention below.

The animal tumor model selected was the Fortner MMI, malignant melanoma grown in the Syrian Golden Hamster. The tumor was grown in the hind flank of each animal. Tumors were allowed to grow for 21 days prior to radiation or injection of test substances. Tumors were passaged by seeding each animal with either a small piece of tumor obtained from a previously grown tumor or by injecting $10^6$ tumor cells harvested from tissue culture. All tumors were injected subcutaneously into the right hind flank of each animal using sterile procedures.

Tumor growth volumes were determined daily. The length (l), width (w), and depth (d) of the tumor was measured using a vernier caliper, and the volume of the tumor was calculated assuming that the tumor shape approximated that of ellipsoid according to the following formula:

$$\text{volume} = \frac{l \times w \times d}{2}$$

Figure 1:
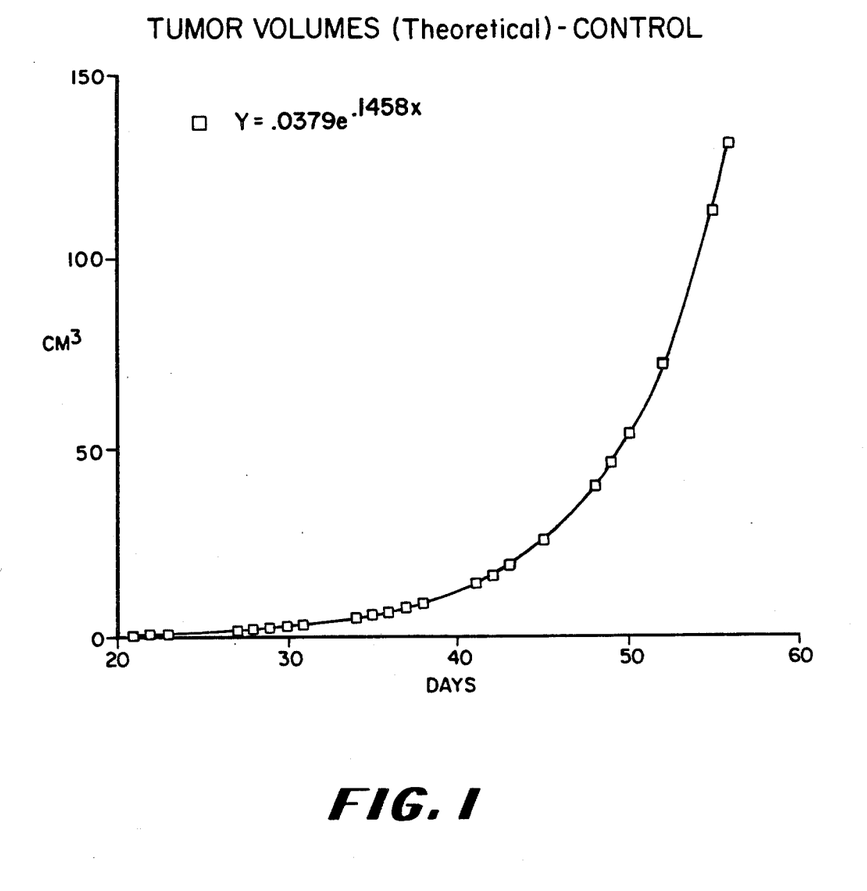
FIG. 1 represents a graph of tumor volume versus days post transplant in untreated animals demonstrating the control group without any treatment of tumors.

Results of the tumor growth are represented in FIG. 1 which plots the average tumor (n=21) volume versus days. Assuming simple exponential growth, a least square analysis of the natural log of the tumor volumes versus days was calculated using a computer program. Good correlation was obtained (R=0.98) with the equation of the line that best approximates normal tumor growth in the animal model as follows.

$$Y = Ae^{bx}$$

where $Y$ = average ln of tumor vol $A$ = $y$ intercept $b$ = growth rate or slope $x$ = time, days (normal tumor growth parameters)

$A$ = 3.39

$b$ = 0.146

Tumor doubling time = $\frac{.693}{b}$ tumor doubling time = 4.7 days

These results represent the control study of normal tumor growth animals not treated with radiation FIG. 1.

Figure 2:
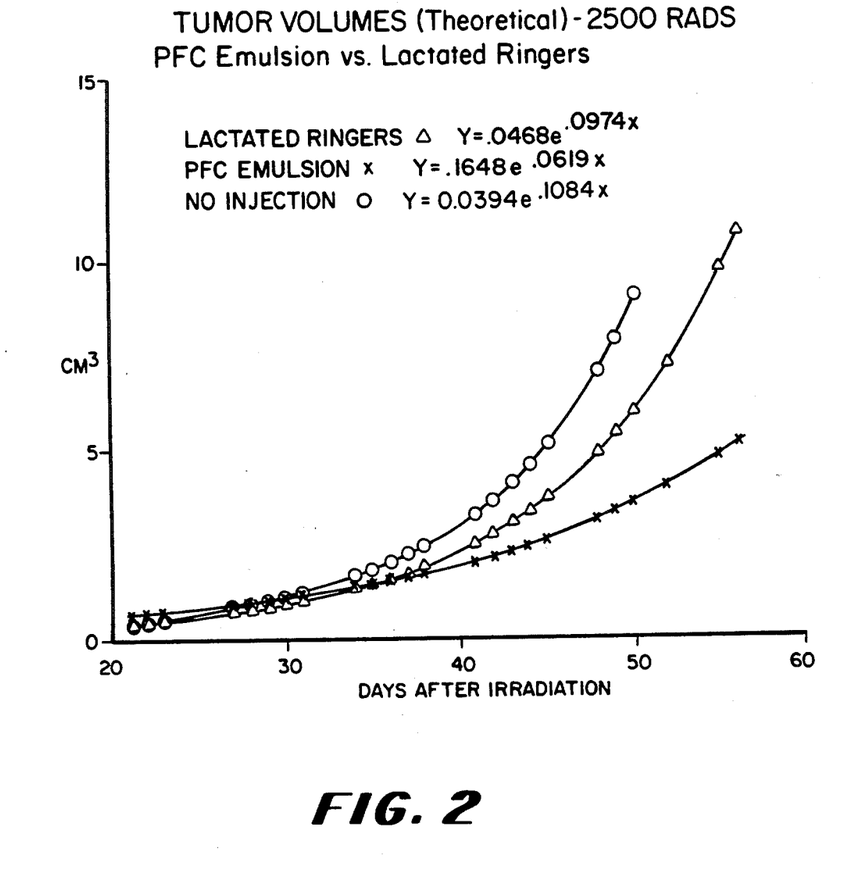
FIG. 2 represents a comparison of tumor treatment without perfluorochemical and with perfluorochemical demonstrating improved tumor growth control for the latter treatment.

Next, groups of animals (n=5) were seeded with tumors and after 21 days were irradiated with either 500, 1500, or 2500 rads of X-ray radiation. The animals were anesthetized during the radiation procedure. Only the tumor in the flank was irradiated through use of a specially constructed jig which allowed placement of the tumor directly into the radiation beam. The animals were administered 10 MeV photons from a Clinac 18 Therapy machine. After radiation, the tumor volumes were determined daily post radiation. These results are shown in FIG. 2 as the radiation control without injection.

Using the same analysis of the tumor growth data, it was determined that 500 rads had no effect on tumor doubling time. Increasing the radiation dose to 1500 rads, resulted in a marginal decrease in the growth rate (increase in doubling time was demonstrated), while at 2500 rads, a significant therapeutic reduction in the growth rate from the average doubling time increasing to 6.4 days. As a result of these tests, it was decided to administer a radiation dose of at least 2500 rads to the tumor, while evaluating the effectiveness of oxygenation using interstitial direct injection of the oxygenated fluoro chemical emulsion into the hypoxic zone of the respective tumors. It is possible to administer a radiation dose up to 5000 rads.

Another group of animals (n=5) were seeded with tumors using the same procedure described above. After 21 days, the tumors were injected interstitially with oxygenated lactated Ringer's solution not containing fluoro chemicals using a 1-½ inch 21 gauge needle. The volume of solution administered was equivalent to 50% of the calculated tumor volume obtained on the day of the test. An oxygenated lactated Ringer's solution was measured to contain two (plus or minus 0.2) milliliters of oxygen per 100 milliliters solution. Within five to ten minutes after injection of the solution, the tumors were irradiated with 2500 rads (25 Gy) of 10 MeV photons. The results of this radiation control are shown in FIG. 2.

Figure 3:
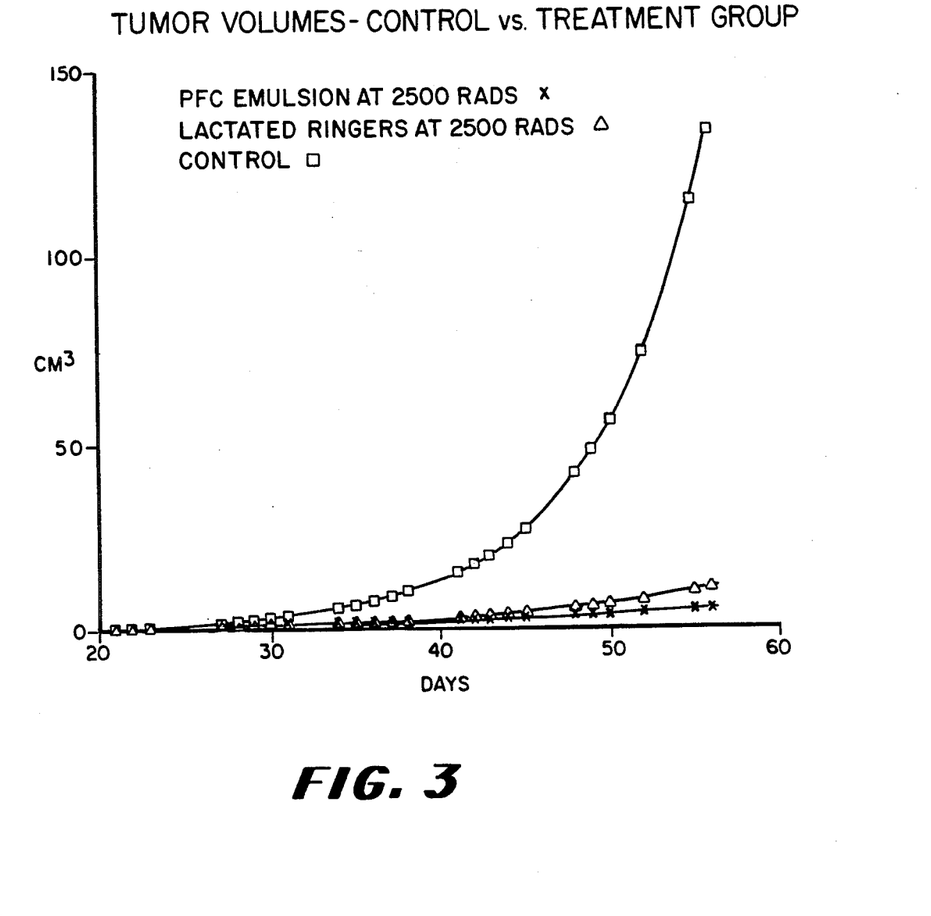
FIG. 3 represents a comparison of the control of FIG. 1 and the treatments illustrated in FIG. 2.

Finally, the experimental demonstration of the subject invention consisted of injecting interstitially the fully oxygenated fluoro chemical emulsion directly into the tumors of similarly treated hamsters. Procedures and methods were identical to those described above. This study was performed at the same time as the study on animals injected merely with Ringer's solution and irradiated on the same day during a one hour time span. Tumor growth was measured as previously described. The results indicate that tumor growth rate was significantly reduced compared to tumors injected with only oxygenated lactated Ringer's solution and irradiated. The results of the subject invention are also shown in FIG. 2, as identified, and the overall results are compiled in FIG. 3. The average tumor doubling time increased to 11.2 days for the present invention. Table 2 summarizes the results of the control and subject invention experimental confirmation studies. In addition, the mean survival time was also determined for each group of animals. The survival time is defined as the length of time it takes an animal to die from the tumor after initial seeding. In some instances the animals would cannablize the tumors, and therefore, some of these animals were removed and counted as dead. The mean survival times for the animals was the greatest in animals treated with both the perfluoro chemical emulsion and radiation.

TABLE 2

| Treatment Protocol | Animals In Study | Mean Tumor Doubling Time (days) | Mean Survival Time (days) |
|---|---|---|---|
| Untreated | 21 | 4.7 | 42 |
| 2500 rads | 11 | 6.4 | 58 |
| 2500 rads + Ringer's (oxygenated) | 5 | 7.1 | 54 |
| 2500 rads + PFC/Ringer's (oxygenated) | 5 | 11.2 | >70 |

As can be seen from Table 2, the tumor treated in the manner of the present invention showed significantly increased survival time and increased tumor doubling time, meaning that it took significantly longer for tumors to reach equivalent sizes. The present understanding of these studies is that the fluorochemical emulsion system transports sufficient quantities of oxygen via small micro particles directly to hypoxic regions within the tumor volume, through the extra cellular space. The extra oxygen carried by the emulsion particles equilibrates with regions of low oxygen tension (hypoxic cells) by diffusion, thereby raising the oxygen tension towards normal or higher levels. These cells revert to normal oxygen metabolism instantly, and therefore are more receptive to cell kill by radiation. The key feature to this invention is the direct interstitial administration of pre-oxygenated perfluoro chemical emulsion into the hypoxic zone of the tumor. This method delivers the greatest amount of oxygen directly to the critical portion of the tumor without dilution from the vascular pool and accordingly reoxygenates the subpopulations of the hypoxic tumor cells for more effective radiation cell kill. This is evident as a significant increased tumor doubling time and greater mean survival over the control test, as described in and identified above. This differs from the prior art which depends on oxygen uptake from the lungs or the blood in the vascular system. The present invention allows a more concentrated and directed use of an oxygen carrier to assist radiation therapy without administering undue total quantities of the fluorochemical emulsion to the patient. It is recognized that administering large fluorochemical emulsion quantities to a patient has detrimental effects on the patient's biological system. The McIntosh reference, cited earlier, addresses this detriment at page 9, line 8, while McIntosh at page 9, line 12 teaches away from administration of less than 2 ml/kg of body weight because no beneficial effect was evidenced. The Yuhas, et al. reference also discloses the lethal effect of high fluorochemical emulsion administration levels, see Example 5. p.25. Yuhas, et al. uses 20–60 ml/kg of body weight.

In contrast the present invention uses only up to 0.055 ml/kg of body weight of fluorochemical emulsion to gain a therapeutic effect while avoiding the toxicity problems of larger dosages.

The present invention has been set forth in one preferred embodiment, but the scope of the invention should be ascertained from the claims which follow.

We claim:

1. A method of treating hypoxic mammalian tumor cells in vivo in a mammal comprising administering an oxygenated fluorochemical emulsion interstitially directly into the hypoxic zones within said tumor and thereafter subjecting the administered cells to an amount of radiation effective to initiate destruction of said cells.

2. The method of claim 1 wherein the fluorochemical is a perfluorocarbon.

3. The method of claim 1 wherein the emulsion is injected interstitially directly into the hypoxic zone of the tumor.

4. The method of claim 1 wherein the radiation comprises X-rays.

5. The method of claim 1 wherein the fluorochemical is selected from the group consisting of perfluoroperhydrophenanthrene, perfluoro n-butyl decalin and mixtures thereof.

6. The method of claim 1 wherein the emulsion comprises a perfluorocarbon with a vapor pressure less than 5 torr selected from partially or fully condensed $C_9$–$C_{14}$ perfluoro compounds present in the emulsion in a concentration of 10-90 weight/volume percent, a surfactant selected from the group of lecithins, acetylenic diols, polyoxyethylenes polyoxypropylene polymers, a mixture of lecithin, glycerin and triglycerides or combinations of the above surfactants with the remainder of the emulsion being an aqueous phase wherein the emulsion has a particle size range of 0.005 to 0.20 microns.

7. The method of claim 1 wherein the radiation dose is above approximately 500 up to approximately 2500 rads.

8. The method of claim 1 wherein the radiation is administered up to 15 minutes after the administration of the emulsion.

9. The method of claim 1 wherein the mammal being subjected to radiation is anesthetized.

10. The method of claim 1 wherein the fluorochemical emulsion is administered in a range of approximately 0.009 to 0.055 ml/kg of body weight.

11. The method of claim 1 wherein the emulsion is saturated with oxygen by bubbling oxygen-enriched gas through said emulsion.

12. The method of claim 1 wherein the administered cells are subjected to a plurality of radiation treatments.

13. The method of claim 1 wherein the cells are subjected to a series of emulsion administrations and subsequent radiation treatments.

14. The method of claim 1 wherein the fluorochemical emulsion is administered in a dosage up to the equivalent of 50% of the tumor volume, but less than 2 ml/kg of body weight.

15. A method of decreasing hypoxic mammalian tumors in vivo in a mammal comprising the interstitial injection of an oxygenated perfluorocarbon $C_{14}$ compound emulsion, having a particle size in the range of 0.005-0.08 microns and a perfluorocarbon content in the range of 25-75 weight/volume percent in a dosage up to the equivalent of 50% of the tumor volume, but less than 2 ml/kg of body weight, directly into the hypoxic zones of said tumor and exposing said tumor to X-ray radiation in an exposure range of above approximately 500 up to 2500 rads within 15 minutes of injection of said emulsion to delay growth of said tumor or decrease the tumor size.

16. The method of claim 15 wherein the emulsion comprises an 85% perfluoroperhydrophenanthrene-15% perfluoro n-butyldecalin mixture in a 67 wt/volume % emulsion of egg yoke lecithin in lactated Ringer's solution.

17. The method of claim 15 wherein the emulsion is saturated with oxygen by bubbling oxygen-enriched gas through said emulsion.

* * * * *

REEXAMINATION CERTIFICATE (1306th)

United States Patent [19]
Schweighardt et al.

[11] B1 4,781,676
[45] Certificate Issued  Jun. 12, 1990

[54] INTERSTITIAL ADMINISTRATION OF PERFLUOROCHEMICAL EMULSIONS FOR REOXYGENATION OF HYPOXIC TUMOR CELLS

[75] Inventors: Frank K. Schweighardt, Allentown; David V. Woo, Downingtown, both of Pa.

[73] Assignee: Air Products and Chemicals, Inc., Allentown, Pa.

Reexamination Request:
No. 90/001,768, May 3, 1989

Reexamination Certificate for:
Patent No.: 4,781,676
Issued: Nov. 1, 1988
Appl. No.: 16,812
Filed: Feb. 20, 1987

[51] Int. Cl.$^5$ .............................. A61N 1/30
[52] U.S. Cl. ........................ 604/21; 604/51; 128/362; 128/804; 514/34; 600/1
[58] Field of Search ................... 604/19–21, 604/49, 51; 128/362, 422; 600/1, 3, 4, 7, 8, 804, 898; 424/320–325; 514/34

[56] References Cited

U.S. PATENT DOCUMENTS

| | | | |
|---|---|---|---|
| 3,911,138 | 10/1975 | Clark | 424/352 |
| 3,962,439 | 6/1976 | Yokoyama et al. | 424/248 |
| 3,993,581 | 11/1976 | Yokoyama et al. | 252/312 |
| 4,443,480 | 4/1984 | Clark | 424/352 |
| 4,742,050 | 5/1988 | Yuhas et al. | 514/34 |

FOREIGN PATENT DOCUMENTS

0201275 12/1986 European Pat. Off. .
23508 9/1985 Taiwan .

OTHER PUBLICATIONS

Hong et al, Journal of Radiation Oncology, Biology, Physics, vol. 10, No. 12, (1984) pp. 2369–2373.
Ohno et al, Journal of Radiation Research, vol. 18, (1977) pp. 275–279.
Sealy et al, Cancer, vol. 54, 10/15/84, pp. 1535–1540.

*Primary Examiner*—Stephen C. Pellegrino

[57] ABSTRACT

A method is set forth for treatment of hypoxic tumors by interstitial injection of oxygen bearing fluorocarbon emulsions directly into the hypoxic zone of the tumor followed by radiation treatment.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 15, 16 and 17 is confirmed.

Claim 14 is cancelled.

Claims 1 and 10 are determined to be patentable as amended.

Claims 2-9 and 11-13, dependent on an amended claim, are determined to be patentable.

1. A method of treating hypoxic mammalian tumor cells in vivo in a mammal comprising administering an oxygenated fluorochemical emulsion *in a dosage up to the equivalent of 50% of the tumor volume, but less than 2 ml/kg of body weight* interstitially directly into the hypoxic zones within said tumor and thereafter subjecting the administered cells to an amount of radiation effective to initiate destruction of said cells.

10. [The method of claim 1 wherein the fluorochemical emulsion is administered] *A method of treating hypoxic mammalian tumor cells in vivo in a mammal comprising administering an oxygenated fluorochemical emulsion* in a range of approximately 0.009 to 0.055 ml/kg of body weight *interstitially directly into the hypoxic zones within said tumor and thereafter subjecting the administered cells to an amount of radiation effective to initiate destruction of said cells.*

* * * * *